United States Patent [19]
Godin

[11] Patent Number: 5,861,036
[45] Date of Patent: Jan. 19, 1999

[54] MEDICAL PROSTHESIS FOR PREVENTING GASTRIC REFLUX IN THE ESOPHAGUS

[75] Inventor: Norman Godin, Geneva, Switzerland

[73] Assignee: Biomedix S.A. Switzerland, Switzerland

[21] Appl. No.: 913,768

[22] PCT Filed: Feb. 28, 1996

[86] PCT No.: PCT/IB96/00149

§ 371 Date: Sep. 23, 1997

§ 102(e) Date: Sep. 23, 1997

[87] PCT Pub. No.: WO96/29954

PCT Pub. Date: Oct. 3, 1996

[30] Foreign Application Priority Data

Mar. 28, 1995 [CH] Switzerland .............................. 866/95

[51] Int. Cl.$^6$ .......................................................... A61F 2/04
[52] U.S. Cl. ............................................... 623/12; 623/11
[58] Field of Search ............................... 623/1, 2, 11, 12, 623/9; 600/37

[56] References Cited

U.S. PATENT DOCUMENTS

| | | | |
|---|---|---|---|
| 4,271,827 | 6/1981 | Angelchik | 600/37 |
| 4,716,900 | 1/1988 | Ravo et al. | 623/12 |
| 4,719,916 | 1/1988 | Ravo | 623/12 |
| 4,846,836 | 7/1989 | Reich . | |
| 4,957,508 | 9/1990 | Kaneko et al. | 623/12 |
| 5,019,102 | 5/1991 | Hoene . | |
| 5,306,300 | 4/1994 | Berry | 623/12 |
| 5,314,473 | 5/1994 | Godin . | |
| 5,411,552 | 5/1995 | Andersen et al. | 623/2 |
| 5,413,601 | 5/1995 | Keshelava | 623/12 |
| 5,662,713 | 9/1997 | Andersen et al. | 623/1 |

FOREIGN PATENT DOCUMENTS

| | | |
|---|---|---|
| 275 535 | 7/1988 | European Pat. Off. . |
| 1 576 374 | 8/1969 | France . |
| 2 513 111 | 3/1983 | France . |
| 1 600 785 | 10/1990 | U.S.S.R. . |
| 1600-785 A | 10/1990 | U.S.S.R. .................................. 623/12 |
| 89 05127 | 6/1989 | WIPO . |
| 91 01117 | 2/1991 | WIPO . |

OTHER PUBLICATIONS

Y. Mizumoto et al, "Trial Use of a Gore–Tex Covered Ultraflex Stent with Reflux Preventive Action for Cardioesophageal Cancer", (Unknown date).

J. Valbuena, "Palliation of Gastroesophageal Carcinoma with Endoscopic Insertion of a New Antireflux Prosthesis", Gastrointestinal Endoscopy, vol. 30, No. 4 1984, pp. 241–243.

Database WPI, Week 9131 23 Oct. 1991; Derwent Publications Ltd., AN 91–265598 XP002008482, & SU,A, 1 600 785; Oct. 23, 1990, see abstract; figure.

*Primary Examiner*—Michael J. Milano
*Assistant Examiner*—Tram A. Nguyen
*Attorney, Agent, or Firm*—Cushman Darby & Cushman Intellectual Property Group of Pillsbury Madison & Sutro, LLP

[57] ABSTRACT

A prosthesis in the form of a flexible tube having a substantially uniform cross section is disclosed. The prosthesis comprises a flange (2) for endoscopically placing stitches or clips in a hiatal hernia (3), and a flexible tubular portion (1) enabling the tube to be squeezed by exerting a pressure (F) on the outer surface thereof in order to prevent reflux of the stomach contents into the esophagus. Food can pass freely through the prosthesis in the direction from the esophagus (4) to the stomach (5). The prosthesis is made of a biocompatible polymer optionally containing barium sulphate to make it detectable using X-rays.

8 Claims, 1 Drawing Sheet

MEDICAL PROSTHESIS FOR PREVENTING GASTRIC REFLUX IN THE ESOPHAGUS

This application is the national phase of international application PCT/IB96/00149, filed Feb. 28, 1996 which designated the U.S.

BACKGROUND OF THE INVENTION

1. Field of the Invention

The present invention relates to a medical prosthesis stopping gastric content from refluxing into the esophagus, including a tube made in a biocompatible polymer material resistant to gastric acid. One end is attached above the stomach and the other one is left free in the stomach.

2. Discussion of the Related Art

This type of prosthesis, described in WO91 01117, describes the shape of a valve with an opening passage kept closed elastically. The section of the passage is progressively narrowed to a permanent shape so as to close the lower end of the tube so that in a position of maximum opening, the section is approximately as wide as the upper end attached to the lower end of the esophagus. This is a description of a valve that is opened by a force capable of overcoming the elastic forces that tend to keep it closed. Such a concept implies a relatively rigid prosthesis that will allow its closure in the absence of any force capable of opening it, this force being generated by the peristaltic pressure exerted on the food bolus by the esophagus.

This solution is unsatisfactory as it creates a situation that is contrary to what naturally occurs, so that the peristaltic pressure has to open the valve.

In certain cases, for example when food is swallowed that has not been sufficiently chewed, an increased force is necessary to allow passage of the food bolus through the esophagus and if a further force is necessary to open the valve, there is either a risk of blocking food or of causing pain or both.

SUMMARY OF THE INVENTION

The aim of the present invention is to overcome, at least in part, the flaws of the abovementioned solution.

We have noticed that another solution, significantly different from the previous one, although at first sight it may appear similar, allows to obtain an equivalent result without the abovementioned flaws. This concept is based on a simple soft tubular element of a fairly constant section which will prolong the esophagus into the stomach. As the stomach has an asymetrical shape in relationship to the axis of the esophagus, in case of gastric reflux, the exerted pressure has a oblique direction in relationship to the axis of the esophagus. Therefore, if one prolongs the esophagus with a soft tube extending for a certain length into the stomach, in case of gastric reflux the soft tube collapses under the oblique pressure and stops the exit of gastric acid into the esophagus.

To this end, the subject of this invention is a medical prosthesis for preventing gastric reflux in the esophagus, including a tube made of a biocompatible polymer that is resistant to gastric acids, one end of which is implanted at the upper opening of the stomach while the other hangs freely below it in the stomach cavity, characterized in that the tube has a section diameter between 25 and 30 millimeters from one end to the other and that its length ranges between 5 and 10 centimeters, the thickness of the wall has been chosen to allow it to collapse under lateral pressure applied to its external wall, when the level of pressure generated by gastric reflux is reached.

Besides the advantages already mentioned, the medical prosthesis which is the object of this invention is easier to introduce into the esophagus with an endoscope because of its increased softness; the prosthesis is also easier to attach in place for the same reasons. As the tubular prosthesis is normally open, contrary to the abovementioned valve which is normally closed, the force exerted on the means used to implant this prosthesis on the walls of the esophagus or of a hiatus hernia is very much decreased, as the only force exerted on the prosthesis is a low friction force of the food bolus on the walls of the prosthesis.

DESCRIPTION OF THE PREFERRED EMBODIMENTS

Figure 1:
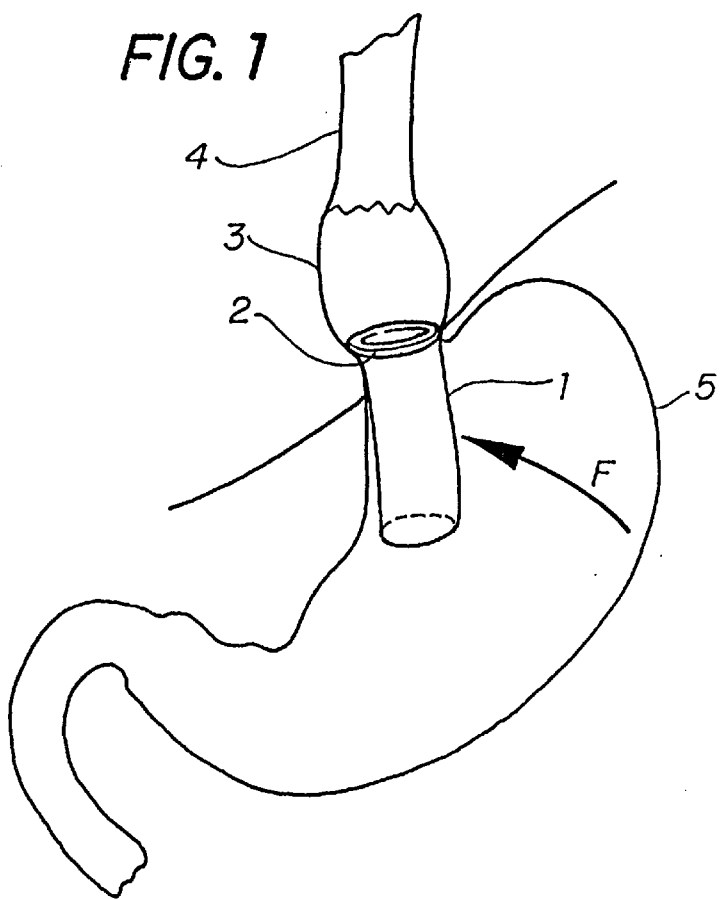
FIG. 1 is a sectional view of the stomach and the esophagus with the prosthesis that is the subject of the present invention.
Figure 2:
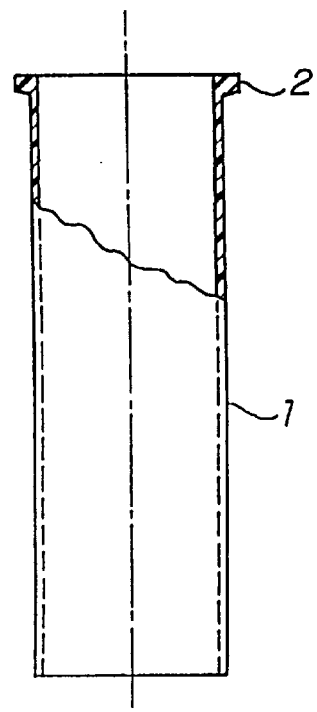
FIG. 2 is a sectional view of the prosthesis of FIG. 1.

The prosthesis illustrated by the FIGS. 1 and 2 is a simple soft tube 1 made in a biocompatible polymer. One can consider several different polymers such as silicone specifically made for medical applications, polyurethanes made for medical applications, polystyrene-ethylene (PSE) or other elastomers, this list is not limitative. The biocompatible polymer from which the prosthesis is made optionally contains barium sulphate to make it detectable using x-rays.

The dimensions of this tube are for example between 25 and 30 mm in diameter. This can vary depending on the diameter of the hiatal hernia or of the esophagus where the prosthesis is implanted and 5 to 10 centimeters in length most of which will be in the stomach. The wall thickness depends largely on the nature of the polymer used which will determine its flexibility but it varies generally between approximately 0.2 and 0.6 mm. This tube must be flexible but must also offer a certain resistance so that it will not turn inside out at pressures under reflux pressures. However, at higher pressures such as in vomiting, it is preferable for the tube to turn inside out. In this case, which is rare, the flexibility of the tube will allow it to return to its original position thanks to peristaltic pressures or an endoscopic intervention could be necessary to position the prosthesis back correctly.

As illustrated in FIG. 1, in the case of increased pressure in the stomach 5, a force is exerted as described by arrow F. That is, the force has an oblique direction in relationship to the long axis of the tube 1 so that with a flexible wall, the tubular prosthesis will collapse against the stomach wall and will stop the gastric acid from leaving the stomach and reaching the mucosa of the esophagus.

On FIG. 1 the tubular prosthesis has a flange 2 attached with sutures or surgical staples to the basis of a hiatus hernia 3 which is one of the essential factors facilitating gastric reflux: the prosthesis can also be attached to the basis of the esophagus 4. Sutures or staples in metal or nylon can be used to bind the prosthesis with appropriate endoscopic suturing equipment.

The tubular prosthesis 1 can be manufactured using several different techniques depending on the biomaterial used, particularly depending on the viscosity of the biomaterial and the thickness of the wall of the prosthesis. The prosthesis can be manufactured by injection molding, extrusion molding or by solvent casting, which is a method of dipping the prosthesis in a solution of the biomaterial until the desired thickness of the wall is obtained. If one uses injection molding, it is preferable to design a cone like shape of approximately 1° or 2° in order to facilitate easy removal of the mold.

Figure 3:
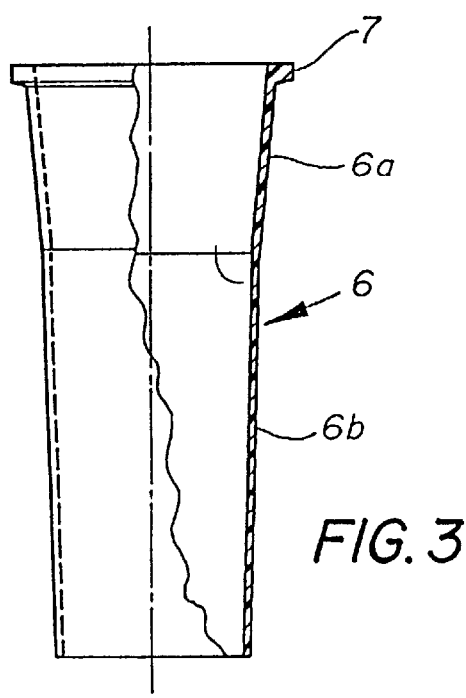
FIG. 3 is a sectional view of a variant of the prosthesis of FIG. 2.

The variant illustrated by FIG. 3 demonstrates an injected tubular prosthesis 6, composed of a thicker flange at one extremity so as to solidify the wall of the device at the point of fixation.

In FIGS. 1 and 2, the tubular prosthesis obtained by injection moulding has a slight conicity of 1° in order to facilitate demolding.

In the case of the alternative example of FIG. 3, the tubular prosthesis 6 is made of 2 segments, a superior segment, 6a, adjacent to the fixation flange 7 which in this example has 25 mm in length, 3° conicity and a thickness of 0.5 mm, and an inferior segment 6b which has in this example 55 mm in length, 1° conicity and 0.3 mm in thickness. It is this inferior segment 6b which extends into the stomach cavity 5 (FIG. 1) and collapses in case of increased gastric reflux pressure.

The prosthesis that is the subject of this patent application functions as the valve described in WO91 01117 while avoiding the drawbacks of the valve. Its greater flexibility facilitates the introduction and endoscopic implantation of said prosthesis.

I claim:

1. A prosthesis to prevent gastric reflux in the esophagus including a tube (1,6) made of a biocompatible polymer that is resistant to gastric acid, one end of said tube being implanted at the upper opening of the stomach (5), the other end of said tube hanging freely in the stomach cavity, wherein the tube (1,6) has a generally constant sectional diameter of between 25 and 30 mm along substantially the entire length thereof from said one end to said other end and the tube has a length ranging between 5 and 10 cm, a thickness of a wall of the tube (1,6) ranging between 0.2 and 0.6 mm, depending on the nature of the polymer, thereby to collapse under lateral pressure applied thereto externally, when the level of pressure generated by gastric reflux is reached.

2. Prosthesis as defined by claim 1, having an annular flange (2,7) defined at and projecting radially outwardly from said one end for implantation.

3. Prosthesis as defined by claim 1, characterized in that said polymer is medical grade polyurethane.

4. Prosthesis as defined by claim 1, characterized in that said polymer is medical grade silicone.

5. Prosthesis as defined by claim 1, characterized in that said polymer is medical grade polystyrene-ethylene (PSE).

6. Prosthesis as defined by claim 1, characterized in that the tube (1,6) is divided longitudinally in to first and second segments (6a, 6b), said first segment (6a), adjacent the one end of the prosthesis presenting a conicity of approximately 3° and said second segment (6b) with a conicity of approximately 1°, a thickness of the second segment (6b) being less than a thickness of the first segment (6a).

7. Prosthesis as defined by claim 6, characterized in that the second segment (6b) delines approximately two-thirds of a total length of the conduit (6).

8. Prosthesis as defined by claim 7, characterized in that the thickness of the second thickness is approximately half of the segment of the first segment.

* * * * *